United States Patent
Kuznetsov et al.

(10) Patent No.: US 8,159,534 B2
(45) Date of Patent: Apr. 17, 2012

(54) METHOD FOR REMOTE INSPECTION OF TARGET IN MONITORED SPACE

(75) Inventors: Andrey Kuznetsov, St. Petersburg (RU); Igor Gorshkov, St. Petersburg (RU); Valery Averyanov, St. Petersburg (RU)

(73) Assignee: APSTEC, Valetta (MT)

( * ) Notice: Subject to any disclaimer, the term of this patent is extended or adjusted under 35 U.S.C. 154(b) by 0 days.

(21) Appl. No.: 13/120,857

(22) PCT Filed: Nov. 24, 2010

(86) PCT No.: PCT/RU2010/000725
§ 371 (c)(1),
(2), (4) Date: Jul. 19, 2011

(87) PCT Pub. No.: WO2011/065869
PCT Pub. Date: Jun. 3, 2011

(65) Prior Publication Data
US 2011/0261156 A1    Oct. 27, 2011

(30) Foreign Application Priority Data
Nov. 26, 2009 (RU) ...................... 2411504

(51) Int. Cl.
*H04N 13/00* (2006.01)
*H04N 15/00* (2006.01)
*H04N 7/18* (2006.01)
*H05G 1/64* (2006.01)

(52) U.S. Cl. .............. 348/143; 348/42; 348/43; 348/47; 378/98.12

(58) Field of Classification Search .................... 348/42, 348/43, 47, 143; 378/98.12
See application file for complete search history.

(56) References Cited

U.S. PATENT DOCUMENTS

| | | | |
|---|---|---|---|
| 4,234,844 A | 11/1980 | Yukl | |
| 4,651,085 A | 3/1987 | Takashi | |
| 2005/0104603 A1 | 5/2005 | Peschmann | |
| 2008/0212742 A1* | 9/2008 | Hughes | ...................... 378/98.12 |

FOREIGN PATENT DOCUMENTS

| | | |
|---|---|---|
| CA | 2388394 | 5/2002 |
| RU | 2086963 | 8/1997 |
| RU | 2283485 | 2/2006 |
| SU | 131138 | 1/1960 |
| SU | 1800333 | 3/1993 |
| WO | WO 2008070788 | 6/2008 |

* cited by examiner

*Primary Examiner* — Christopher S Kelley
*Assistant Examiner* — Chikaodili E Anyikire
(74) *Attorney, Agent, or Firm* — Nadya Reingand

(57) ABSTRACT

This invention addresses remote inspection of target in monitored space. A three dimensional (3D) microwave image of the space is obtained using at least two emitters. The data undergoes coherent processing to obtain maximum intensity of the objects in the area. This image is combined with a 3D video image obtained using two or more video cameras synchronized with the microwave emitters. The images are converted into digital format and transferred into one coordinate system. The distance l is determined between the microwave and the video image. If $l<l_o$, where $l_o$ is a given threshold, the absence of a concealed dielectric object at the target is indicated. If $l>l_o$ then the presence of cavities is analyzed. If the cavity depth h is greater than the threshold value $h_o$ a concealed dielectric object at the target is ascertained:

$$h_0 = l_0 \frac{\sqrt{\varepsilon}-1}{\sqrt{\varepsilon}}$$

where $\in$ is dielectric permeability of the sought dielectric object.

1 Claim, 2 Drawing Sheets

METHOD FOR REMOTE INSPECTION OF TARGET IN MONITORED SPACE

FIELD OF THE INVENTION

This invention belongs to the field of remote detection of hidden objects, particularly to methods for detection of dielectric explosive substances concealed under clothes on the human body. Foremost among the primary safety and security concerns is the "suicide bomber", who is carrying a bomb on his/her body.

BACKGROUND OF THE INVENTION

Currently, various methods are being used to combat this concern. Some of which include: metal detectors, vapour detectors, X-ray machines, and dogs. Many countries are putting forth great effort in developing new methods for inspection of the human body based on new physical principles: Nuclear Quadrupole Resonance (NQR), Raman backscattering, dielectric portals, passive and active terahertz range devices, passive millimeter range radars and active microwave portals.

The aforementioned methods do not guarantee the required effectiveness of remote and covert inspection, thus, these devices are not capable to detect a "suicide bomber" in adequate time so that the necessary precautions can be taken before detonation of the explosive device. Another notable disadvantage of the currently used methods is non-automatic determination of the threat level of the detected object in addition to the high false alarms' rate. These obstacles make it nearly impossible to use these devices for inspection of a large number of people moving in transit.

Hence, the task of detecting explosive devices being carried by "suicide bombers" should allow for the following provisions:
  Remote inspection;
  Automatic inspection;
  Detection of various types of objects (dielectric/metal objects);
  Detection in real time;
  Automatic system determining threat level of the detected object;
  Covert inspection;
  Independence of external conditions;
  Safety for human health;
  Possibility to bind data and threat signal for a specific individual;
  Mobility and relatively low cost There is a current method of detection used for metallic and non-metallic explosive devices being concealed on a person. In this method, the receiving antenna focuses on a small area of the human body using electromagnetic waves coming from that region. A radiometer data is then processed in a processing module, and the intensity and the position of the beam is recorded. The measured intensity of the received signal is then displayed as luminous intensity. By analyzing the distribution of the luminous intensity, the presence or absence of metallic or non-metallic objects can be determined, see, for example, Russian Patent No. RU2133971.

The main disadvantage of this method is the low contrast of the received image. This method cannot clearly distinguish non-metallic objects from the human body while the dielectric for the used wave range is transparent.

A second method of target remote inspection in monitored space is to irradiate the inspected area with microwaves using two or more elemental emitters. In this method, a register signal is reflected from the monitored area using one or more parallel recording channels. Coherent processing of the reflected signal occurs and the data received is displayed, see, for example, U.S. Pat. No. 5,557,283.

Emitters and receivers of an electromagnetic field are placed in multiple predetermined positions. The final determination is made after analyzing a three-dimensional image received after digital processing of the radiation is recorded in broadband.

This method uses microwaves for irradiation of a monitored area in frequency bandwidth without correlating its width with radial space resolution of the monitored area image and recording the time interval during which coherent processing of the received reflected signal is possible. This brings on the following disadvantages:

The method cannot be used to inspect a moving object/target. When an object is moving in space during the recording of the reflected signal, the position of the object against the emitting/receiving antennas changes thus making it impossible to use coherent processing of the recorded signal. Non-coherent processing results in low resolution imaging if the direction of movement of the inspected object is unknown. Thus, covert inspection is not possible.
  Low resolution imaging cannot be analyzed to obtain quantitative data about the dielectric permeability of objects (parts of the target) and their equivalent mass.

Another method for remote inspection of a target in monitored space includes irradiation of the monitored area with microwaves using two or more elemental microwave emitters and recording the reflected signal from the monitored area using one or more parallel recording channels. Coherent processing of the recorded signal to receive maximal intensity values of restored configuration of scattering objects in the monitored area is dependent upon the distance from the elemental emitters to the target. A display of the information is obtained after processing by reconstructing a microwave image as several three-dimensional surfaces, see Russian Patent No. RU 2294549. The aforementioned technical solution was used as a prototype for the proposed invention.

The main disadvantages of the technical solution which was used as a prototype for the proposed invention are:
  Low intensity of the signal reflected from an "air-dielectric" border—about 7% of intensity for dielectrics with dielectric permeability ~3 (which is typical for explosives). Thus, the signal reflected from the "dielectric-body" border (~90% of intensity) could drastically distort the three-dimensional surface representing the "air-dielectric" border which leads to errors when determining the presence of explosive material;
  Only a small range of microwave radiation incidence and receiving angles in which radiation reflected from the "air-dielectric" border can actually be recorded. Usually this is due to the fact that the dielectric's surface tends to be rather smooth, when compared to the wave length of microwave range and scattering on the border takes the form of mirror reflection. Therefore, this method of inspection is useful only in a very small range of possible angles of inspection.

DETAILED DESCRIPTION

The primary tasks of the proposed invention are to increase the accuracy of determination for the presence/absence of dielectric objects during covert inspection and to enlarge the range of possible views of inspection.

Figure 1:
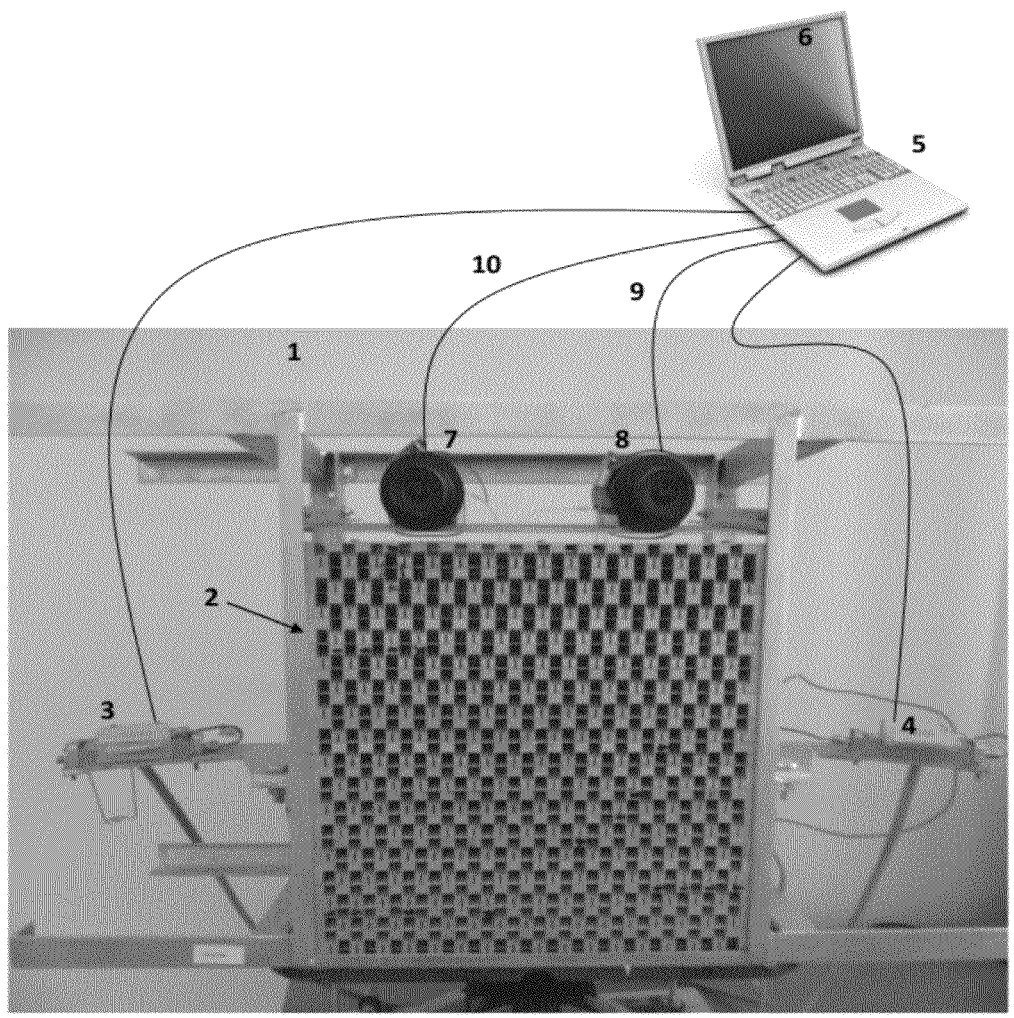
FIG. 1 shows one embodiment of the setup for suicide bomb detection.
Figure 2:
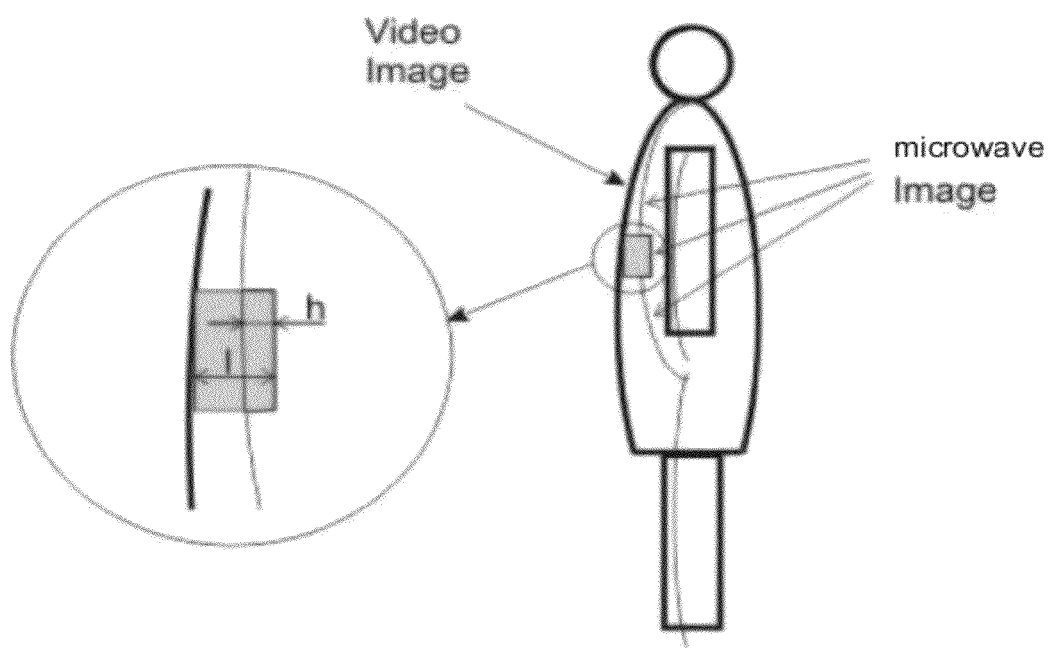
FIG. 2 illustrates the overlapping of the microwave and video images.

One embodiment of a setup 1 for remote inspection of a target in monitored space is shown in FIG. 1. The space is scanned with microwave radiation using two or more elemental microwave emitters 2. The signal reflected from the monitored area is picked up by one or more parallel detection channels 3 and 4. The received signal undergoes coherent processing in digital signal processing unit (DSP) 5 to obtain maximum intensity values of the restored configuration of scattering objects in the monitored area, depending on the distance from the elemental emitters to the target. The information obtained after processing is then displayed on the display 6 by constructing a microwave image corresponding to a three-dimensional surface. A video image of the target is also obtained using two or more video cameras 7 and 8 which are synchronized with the microwave emitters 2 via the processing unit 5. The obtained video images are transmitted via channels 9 and 10 into the processing unit and are further converted to its digital form, and a three-dimensional image of the target is constructed and displayed on the display 6. The three-dimensional video image and the microwave image are then transferred into a general coordinate system. When you are looking at the system 1 at FIG. 1, you are in the position of the person, who is monitored. The mutual positioning of the microwave image (thin line) and the video image (thick line) is shown in FIG. 2.

A method for remote inspection of a target in monitored space is disclosed. The space is scanned with microwave radiation using two or more elemental microwave emitters. The signal reflected from the monitored area is picked up by one or more parallel detection channels. The received signal undergoes coherent processing to obtain maximum intensity values of the restored configuration of scattering objects in the monitored area, depending on the distance from the elemental emitters to the target. The information obtained after processing is then displayed by constructing a microwave image corresponding to a three-dimensional surface. A video image of the target is also obtained using two or more video cameras which are synchronized with the microwave emitters. The obtained video image is converted to its digital form, and a three-dimensional image of the target is constructed. The three-dimensional video image and the microwave image are then transferred into a general coordinate system. The distance l in the general coordinate system is determined, between the microwave image and the video image. If $l<l_o$, where $l_o$ is a given threshold value of l, this indicates the absence of a concealed dielectric object at the target, in an amount which exceeds the maximum allowable value. If $l>l_o$, there is further determination of the presence of cavities in the three-dimensional microwave image in regions where $l>l_o$ and when the depth h of the cavity is greater than $$h_o = l_o(\in^{1/2}-l)/\in^{1/2}$$

where $h_o$ is the threshold value of h, $\in$ - is dielectric permeability of the sought dielectric object. Presence of a concealed dielectric object at the target is ascertained.

Authors of the invention didn't discover any technical decision similar to the proposed invention which allows marking the invention as "Novelty".

Realization of the characteristic features of the invention determines new important parameters of the device. Distortions of the three-dimensional surface representing physical "air-dielectric" borders are corrected, which decreases possibility of errors when determining the presence/absence of an explosive.

Additional usage of the three-dimensional video image enlarges the range of possible angles of inspection.

Authors of the invention didn't discover any informational sources which reveal the possible influence of characteristic features of the invention on technical effect. The listed new characteristic features of the device, according to the authors of the invention, could be marked as "Inventive level".

Realization of the method could be best illustrated with an example. To carry out remote inspection of the target in a monitored area, the area is irradiated by microwave radiation successively at 14 equidistant frequencies in the range 8-12 GHz. Irradiation is made by elemental emitters which in this particular example is a switched antenna array consisting of 256 emitting antennas. The signal reflected from the monitored area is then recorded by two parallel channels including two broadband Vivaldi antennas and two receivers. From receivers' outputs, data about the recorded signal is transferred onto a PC where coherent processing occurs, and imaging of the target is made as of one single, three-dimensional surface consisting of points (which correspond to maximum values of restored configuration of scattering objects in the monitored area depending on the distance from the elemental emitters to the target).

Simultaneously, two additional video cameras (in this example that were two digital spatially separated SDU-415 video cameras synchronized with microwave emitters) recorded a video image of the target received, which was then digitized. The three-dimensional video image of the target is reconstructed on a PC and is later converted into a general system of coordinates general to the video image and microwave image. The system of coordinates is set by the antenna array's plane and is perpendicular to its center. The distance l in the general coordinate system, between the microwave image and the video image is determined. If $l<l_o$, where $l_o$ is a given threshold value of l, this indicates the absence of a concealed dielectric object at the target, in an amount which exceeds the maximum allowable value. If $l>l_o$, there is further determination of the presence of cavities in the three-dimensional microwave image in regions where $l>l_o$ and when the depth h of the cavity is greater than $$h_o = l_o(\in^{1/2}-l)/\in^{1/2}$$

where $h_o$ is the threshold value of h, $\in$ - is dielectric permeability of the sought dielectric object. Most frequently-used explosives have a dielectric permeability of $\in \approx 3$.

Since the three-dimensional image of the "air-dielectric" and "dielectric-body" borders are reconstructed using different physical principles ("air-dielectric" border image is reconstructed using video data, "dielectric-body" border image is reconstructed using received microwave signal), distortion of the "air-dielectric" border by reflected microwave signal is removed. This also minimizes possible errors when determining the presence/absence of an explosive substance.

Moreover, since microwave radiation is not used to reconstruct the "air-dielectric" border, the smoothness of the dielectric surface has no effect and the possible angles of inspection are greater.

The invention claimed is:

1. A method for a remote target inspection in a monitored space, comprising:

scanning the target with microwave radiation using at least two microwave emitters;

collecting radiation reflected back from the monitored area using one or more detectors located to pick up the radiation in parallel channels;

performing coherent processing to obtain maximum intensity values of a target image;

constructing a three-dimensional microwave image;

illuminating the target with optical radiation and recording at least video images of the target using at least two video cameras;

synchronizing the video images with the microwave image;

digitizing the video images and creating a three-dimensional image of the target;

combining the three-dimensional video image and three-dimensional microwave image in one coordinate system;

determining a distance l between the microwave image and the video image;

if l is less than a threshold value $l_o$, then producing a conclusion about an absence of a concealed dielectric object at the target in an amount which exceeds the maximum allowable value;

if l is larger than the threshold value $l_o$, then determining a presence of cavities in the three-dimensional microwave image in regions where $l > l_o$ and when the depth h of the cavity is greater than $h_o = l_o(\in^{1/2} - 1)/\in^{1/2}$ a presence of the concealed dielectric object at the target is ascertained, where $h_o$ is the threshold value of h, $\in$ is assumed dielectric permeability of the dielectric object.

* * * * *